(12) United States Patent
Miyamoto (10) Patent No.: US 10,153,418 B2
(45) Date of Patent: Dec. 11, 2018

(54) CONTROL CIRCUIT OF PIEZOELECTRIC DRIVING DEVICE, PIEZOELECTRIC DRIVING DEVICE, ULTRASONIC MOTOR, ROBOT, HAND, AND PUMP

(71) Applicant: Seiko Epson Corporation, Tokyo (JP)

(72) Inventor: Tsutomu Miyamoto, Shiojiri (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 15/463,409

(22) Filed: Mar. 20, 2017

(65) Prior Publication Data

US 2017/0279029 A1 Sep. 28, 2017

(30) Foreign Application Priority Data

Mar. 22, 2016 (JP) .................. 2016-056604

(51) Int. Cl.
| | |
|---|---|
| *H01L 41/04* | (2006.01) |
| *A61B 34/30* | (2016.01) |
| *B06B 1/06* | (2006.01) |
| *H01L 41/09* | (2006.01) |
| *A61M 5/142* | (2006.01) |
| *H02N 2/14* | (2006.01) |

(52) U.S. Cl.
CPC ............ *H01L 41/042* (2013.01); *A61B 34/30* (2016.02); *A61M 5/14228* (2013.01); *B06B 1/0607* (2013.01); *H01L 41/09* (2013.01); *H02N 2/142* (2013.01); *A61M 5/142* (2013.01); *Y10S 901/19* (2013.01)

(58) Field of Classification Search
CPC ..... B06B 1/0607; H01L 41/042; H01L 41/09; H02N 2/142
See application file for complete search history.

(56) References Cited

U.S. PATENT DOCUMENTS

| 4,939,405 | A | * | 7/1990 | Okuyama | ............ | F04B 43/046 310/317 |
|---|---|---|---|---|---|---|
| 2008/0265714 | A1 | * | 10/2008 | Morioke | .................. | G02B 7/08 310/315 |
| 2013/0307896 | A1 | * | 11/2013 | Shinkawa | .............. | B41J 29/393 347/19 |
| 2014/0125723 | A1 | * | 5/2014 | Otokita | ................... | B41J 2/0451 347/12 |
| 2015/0251415 | A1 | * | 9/2015 | Takagi | ................. | B41J 2/04541 347/10 |

FOREIGN PATENT DOCUMENTS

JP 2008-199774 A 8/2008

* cited by examiner

*Primary Examiner* — Muhammad S Islam
(74) *Attorney, Agent, or Firm* — Harness, Dickey & Pierce, P.L.C.

(57) ABSTRACT

A control circuit of a piezoelectric driving device includes: a signal generation unit that inputs a state inspection signal to a plurality of piezoelectric elements connected to each other in parallel; and a state detection unit that detects a state of the plurality of piezoelectric elements based on a state detection signal generated from the plurality of piezoelectric elements in accordance with the state inspection signal.

11 Claims, 10 Drawing Sheets

CONTROL CIRCUIT OF PIEZOELECTRIC DRIVING DEVICE, PIEZOELECTRIC DRIVING DEVICE, ULTRASONIC MOTOR, ROBOT, HAND, AND PUMP

BACKGROUND

1. Technical Field

The present invention relates to a control circuit of a piezoelectric driving device, a piezoelectric driving device, an ultrasonic motor, a robot, a hand, and a pump.

2. Related Art

In JP-A-2008-199774, a state of a piezoelectric element is determined by a potential difference detection unit that measures a potential difference of both ends of a detection resistor connected to the piezoelectric element, and a state determination unit that determines a state of the piezoelectric element based on the potential difference measured by the potential difference detection unit.

However, in a case where a plurality of piezoelectric elements are provided, it is necessary to provide a plurality of potential difference detection units and state determination units, in order to detect states of the plurality of piezoelectric elements. Accordingly, the configuration thereof becomes complicated and it is difficult to achieve miniaturization.

SUMMARY

An advantage of some aspects of the invention is to solve the problems described above, and the invention can be implemented as the following aspects.

(1) According to an aspect of the invention, a control circuit of a piezoelectric driving device is provided. The control circuit includes: a signal generation unit that inputs a state inspection signal to a plurality of piezoelectric elements connected to each other in parallel; and a state detection unit that detects a state of the plurality of piezoelectric elements based on a state detection signal generated from the plurality of piezoelectric elements in accordance with the state inspection signal.

According to the aspect, it is possible to detect the state of the plurality of piezoelectric elements based on the state detection signal generated from the plurality of piezoelectric elements connected to each other in parallel. In addition, it is possible to realize simplification and miniaturization of a device configuration.

(2) In the control circuit according to the aspect, the state detection signal may be a current flowing to the plurality of piezoelectric elements in accordance with the state inspection signal, and the state detection unit may include a current detection unit that detects a current flowing to the plurality of piezoelectric elements, and acquire an integrated current value when a certain time of an integrated current obtained by integrating the current detected by the current detection unit has been elapsed from the time when the state detection signal in a step-wise shape is input, as a state detection value, and detect the state of the plurality of piezoelectric elements based on the state detection value.

According to the aspect with this configuration, since the integrated current value acquired as the state detection value shows a value that varies depending on the state of the plurality of piezoelectric elements, it is possible to detect the state of the plurality of piezoelectric elements based on the state detection value.

(3) In the control circuit according to the aspect, the state detection unit may detect the state of the plurality of piezoelectric elements, by comparing the state detection value with a determination value showing a state of increasing of the integrated current based on a time constant showing step response characteristics of the plurality of piezoelectric elements.

According to the aspect with this configuration, since the state detection value showing the state of increasing of the integrated current shows a value that varies depending on the state of the plurality of piezoelectric elements, it is possible to detect the state of the plurality of piezoelectric elements by comparing the state detection value with the determination value showing the state of increasing of the integrated current based on the time constant showing step response characteristics of the plurality of piezoelectric elements.

(4) In the control circuit according to the aspect, the state detection unit may include a storage unit that stores a relationship between the state detection value and the determination value.

According to the aspect with this configuration, it is possible to detect the state of the plurality of piezoelectric elements using the determination value stored in the storage unit.

(5) In the control circuit according to the aspect, the state detection signal may be a current flowing to the plurality of piezoelectric elements in accordance with the state inspection signal, and the state detection unit may include a current detection unit that detects a current flowing to the plurality of piezoelectric elements, and acquire an effective current value of the current detected by the current detection unit as a state detection value, when the state detection signal in a sinusoid shape is input to the plurality of piezoelectric elements, and detect the state of the plurality of piezoelectric elements based on the state detection value.

According to the aspect with this configuration, since the effective current value acquired as the state detection value shows a value that varies depending on the state of the plurality of piezoelectric elements, it is possible to detect the state of the plurality of piezoelectric elements based on the state detection value.

(6) In the control circuit according to the aspect, the state detection unit may detect whether the state of the plurality of piezoelectric elements is in any state of a normal state, a short-circuit abnormal state, and a disconnection abnormal state, based on the state detection value.

According to the aspect with this configuration, since the state detection value shows a value that varies depending on whether the state of the plurality of piezoelectric elements is in any state of the normal state, the short-circuit abnormal state, and the disconnection abnormal state, it is possible to detect whether the state of the plurality of piezoelectric elements is in any state of the normal state, the short-circuit abnormal state, and the disconnection abnormal state, based on the state detection value.

(7) In the control circuit according to the aspect, the state detection unit may detect the number of piezoelectric elements in the disconnection abnormal state among the plurality of piezoelectric elements, based on the state detection value.

According to the aspect with this configuration, since the state detection value shows a value that varies depending on the number of the plurality of piezoelectric elements in the disconnection abnormal state, it is possible to detect the number of the piezoelectric elements in the disconnection abnormal state based on the state detection value.

(8) According to another aspect of the invention, a piezoelectric driving device is provided. The piezoelectric driving device includes: a plurality of piezoelectric elements connected to each other in parallel; and the control circuit of any aspect described above.

According to the aspect, it is possible to provide a piezoelectric driving device capable of detecting the state of the plurality of piezoelectric elements included in the piezoelectric driving device.

(9) The piezoelectric driving device of the aspect may further include: a piezoelectric actuator including the plurality of piezoelectric elements, and the plurality of piezoelectric elements may be laminated and disposed in a direction crossing a flat surface where the piezoelectric elements are formed.

According to the aspect with this configuration, since the piezoelectric elements are laminated on each other, a vibrating force can become great.

The invention can be implemented in various aspects, and can be, for example, implemented as various aspects such as an ultrasonic motor, a robot including an ultrasonic motor, a hand including an ultrasonic motor, or a pump including an ultrasonic motor, in addition to the control circuit of the piezoelectric driving device or the piezoelectric driving device.

BRIEF DESCRIPTION OF THE DRAWINGS

The invention will be described with reference to the accompanying drawings, wherein like numbers reference like elements.

DESCRIPTION OF EXEMPLARY EMBODIMENTS

A. First Embodiment

Figure 1:
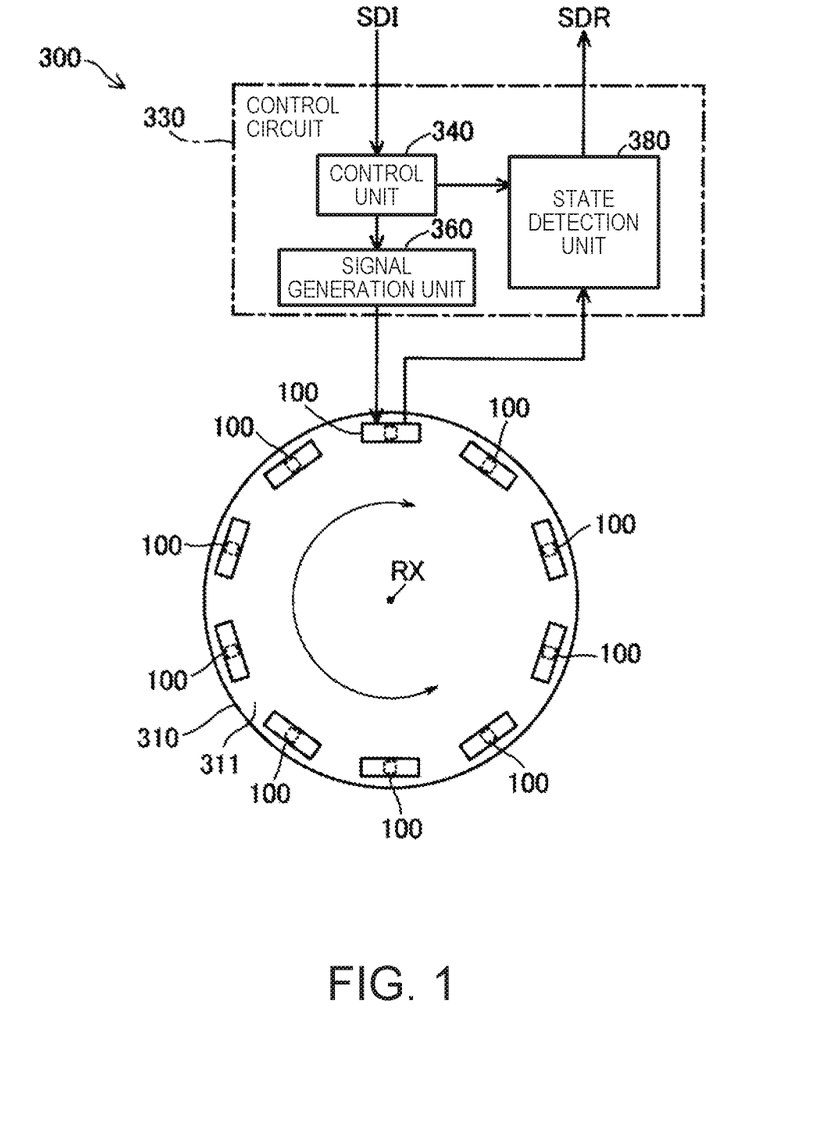
FIG. 1 is an explanatory diagram showing an ultrasonic motor of a first embodiment.

FIG. 1 is an explanatory diagram showing an ultrasonic motor 300 of the first embodiment. The ultrasonic motor 300 includes a rotor 310 as an object to be driven, and a plurality of piezoelectric actuators 100 as piezoelectric driving devices, and a control circuit 330. Each piezoelectric actuator 100 comes into contact with the rotor 310 to cause ultrasonic vibration and to apply a driving force of rotation of the rotor 310. The control circuit 330 causes the ultrasonic vibration and drives the piezoelectric actuators 100. FIG. 1 shows an example in which ten piezoelectric actuators 100 are disposed along a peripheral line of a circular surface 311 orthogonal to a central axis RX of the rotor 310. FIG. 1 only shows one control circuit 330 corresponding to one piezoelectric actuator 100 among the plurality of control circuits 330 that drives the piezoelectric actuators 100, and other control circuits are omitted. Relationships of each of the piezoelectric actuators 100 and the corresponding control circuits 330 are same as each other.

The control circuit 330 includes a control unit 340, a signal generation unit 360, and a state detection unit 380. The control unit 340 controls operations of the signal generation unit 360 and the state detection unit 380 in accordance with an instruction from a host control device (not shown). For example, at the time of normal driving, the signal generation unit 360 is controlled in accordance with an instruction from the host control device, and the piezoelectric actuators 100 are driven to rotate the rotor 310. At the time of inspection which will be described later, the signal generation unit 360 and the state detection unit 380 are controlled in accordance with an instruction SDI of inspection from the host control device to inspect the states of the piezoelectric actuators 100, and an inspection result SDR is output to the host control device.

Figure 2:
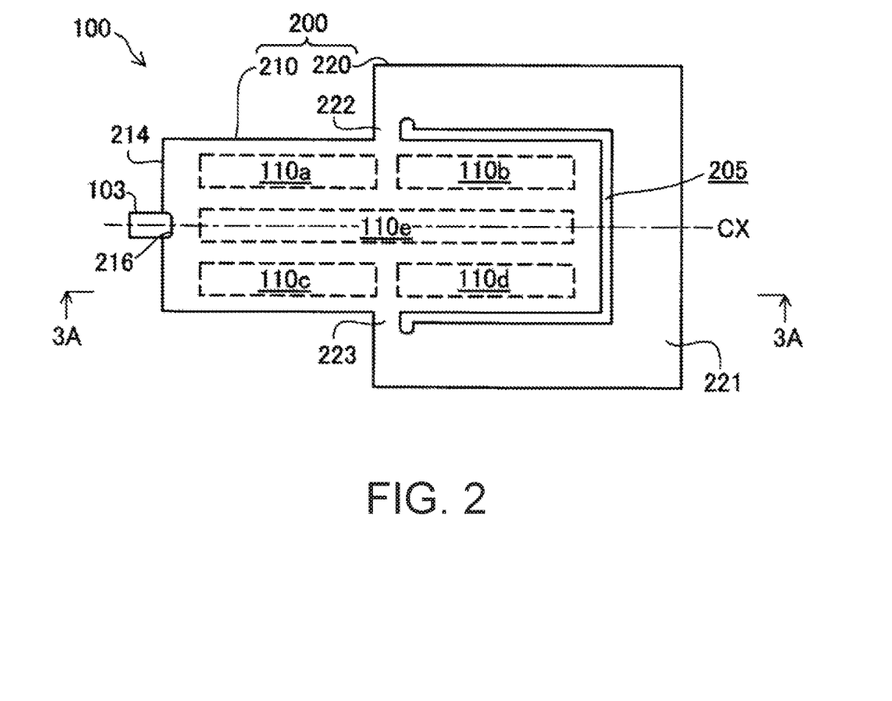
FIG. 2 is an explanatory diagram showing a schematic configuration of a piezoelectric actuator.

FIG. 2 is an explanatory diagram showing a schematic configuration of the piezoelectric actuator 100. The piezoelectric actuator 100 includes piezoelectric elements 110a, 110b, 110c, 110d, and 110e as vibrators, a substrate 200 as a vibrating plate, and a protrusion 103. The substrate 200 includes a vibrating portion 210 and a support 220. The vibrating portion 210 has an approximately rectangular shape and the piezoelectric elements 110a to 110e are disposed thereon. The piezoelectric element 110e is configured to have an approximately rectangular shape, and is disposed in the center of the vibrating portion 210 in a short direction (also referred to as a "short side direction" or a "width direction") along a longitudinal direction (direction along a central line CX) of the vibrating portion 210. The piezoelectric elements 110a to 110d are disposed at positions of four corners of the vibrating portion 210.

The support 220 is disposed so as to surround approximately half of the vibrating portion 210, and end portions of the support 220 are connected to the vibrating portion 210 at the center of a long side of the vibrating portion 210. End portions of the support 220 connected to the vibrating portion 210 are referred to as a "first connection portion 222" and a "second connection portion 223", and a portion thereof other than the first connection portion 222 and the second connection portion 223 is referred to as a "fixed portion 221". A gap 205 is disposed between the vibrating portion 210 and the support 220. When a voltage is applied to the piezoelectric elements 110a to 110e, the piezoelectric elements 110a to 110e expand and contract, and the vibrating portion 210 is vibrated, but the gap 205 is configured to have a size so that the vibrating portion 210 does not come into contact with the fixed portion 221 of the support 220 even with this vibration. The protrusion 103 is provided on a recess 216 at a center position (position on the central line CX in a plan view) of a side surface 214 including a short side at a side of the vibrating portion 210 not surrounded by the support 220. The protrusion 103 is preferably configured with a material having durability such as ceramic (for example, $Al_2O_3$).

Figure 3:
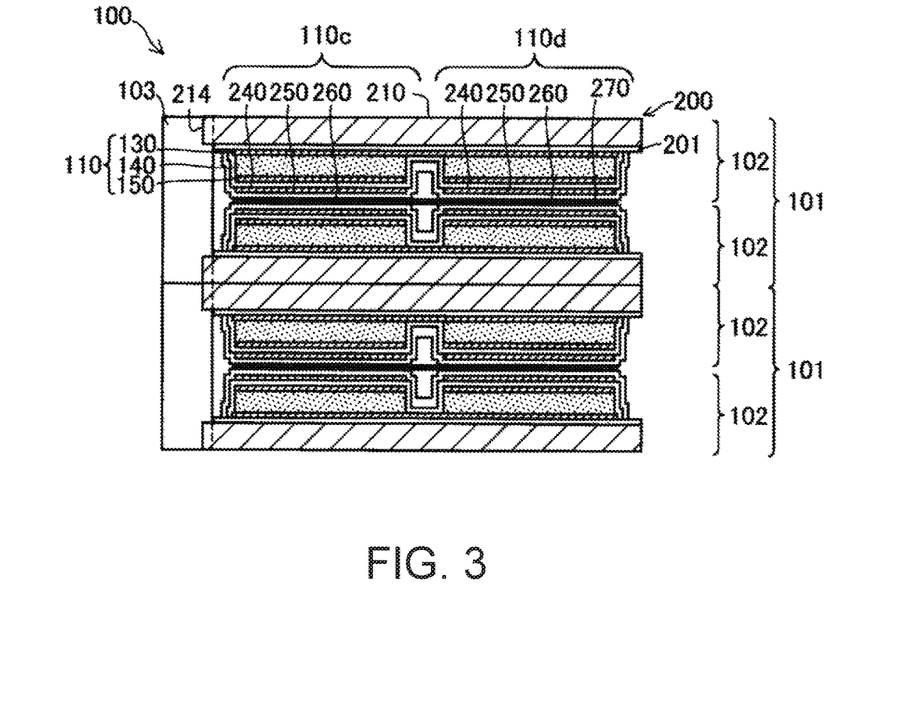
FIG. 3 is a sectional view of the piezoelectric actuator.

FIG. 3 is a 3A-3A sectional view of the piezoelectric actuator 100 of FIG. 2. In FIG. 3, for convenience of illustration of drawings, dimensions in a vertical direction (thickness direction) are enlarged. FIG. 3 shows only a cross section corresponding to the vibrating portion 210. A cross section corresponding to the fixed portion 221 also has the same structure as that of the vibrating portion 210.

As shown in FIG. 3, the piezoelectric actuator 100 includes two piezoelectric vibrator units 101 laminated on each other. The piezoelectric vibrator unit 101 includes two piezoelectric vibrators 102 laminated on each other. Each of the two piezoelectric vibrators 102 includes the substrate 200 and the five piezoelectric elements 110a to 110e (FIG. 2) disposed on the substrate 200. Since FIG. 3 is a 3A-3A sectional view of FIG. 2, and shows two piezoelectric elements 110c and 110d among the five piezoelectric elements 110a to 110e, and other three piezoelectric elements 110a, 110b, and 110e are not shown. Each of the piezoelectric elements 110a to 110e includes a first electrode 130, a piezoelectric body 140, and a second electrode 150. The piezoelectric elements 110a to 110e are respectively disposed on a flat surface (main surface) at a side where two substrates 200 face each other, in a region (region of the vibrating portion 210) in which the two substrates 200 are superposed on each other in a plan view (see FIG. 2). Two piezoelectric elements using the same reference numeral, for example, two piezoelectric elements 110a are at a position where the piezoelectric elements are seen to be superimposed on each other in a plan view of the two substrates 200. The same applies to the other piezoelectric elements 110b to 110e.

The two piezoelectric vibrators 102 are disposed so that the piezoelectric elements 110a to 110e are interposed between the two substrates 200 by disposing the substrates 200 on the outer side. That is, in the piezoelectric vibrator unit 101, the two piezoelectric vibrators 102 are disposed (laminated on each other) on the substrate 200 along a direction in which the piezoelectric elements 110a to 110e are disposed. Each of the piezoelectric elements 110a to 110e are covered with a protective layer 260. Here, the "protective layer 260" is also referred to as a "coating portion 260". The coating portions 260 of the two piezoelectric vibrators 102 are bonded to each other with an adhesive layer 270, and accordingly, the piezoelectric vibrator unit 101 is configured. As shown in FIGS. 2 and 3, the protrusion 103 has an approximately rectangular parallelepiped shape and is attached over the two substrates 200. However, the protrusion 103 may have an approximately columnar shape, a spherical shape, or an elliptical shape or may be provided on each of the substrates 200. The piezoelectric vibrator 102 corresponds to one "vibrator".

In the piezoelectric vibrator 102, each member is disposed on the substrate 200 in the order of an insulating layer 201, the first electrode 130, the piezoelectric body 140, the second electrode 150, an insulating layer 240, a wiring layer 250, and the protective layer 260 (coating portion 260). The insulating layer 201 insulates the substrate 200 from the other electrodes (first electrode 130, the second electrode 150, and the wiring layer 250). The first electrode 130, the piezoelectric body 140, and the second electrode 150 configure the piezoelectric elements 110a to 110e. The insulating layer 240 covers and insulates the piezoelectric elements 110a to 110e. However, the insulating layer 240 includes a contact hole for bringing the first electrode 130 and the second electrode 150 of the piezoelectric elements 110a to 110e to come into contact with the wiring layer 250. In the wiring layer 250, a wiring to be electrically connected to the first electrode 130 and the second electrode 150 is disposed. As described above, the protective layer 260 protects the piezoelectric elements 110a to 110e.

The piezoelectric vibrator 102 can be manufactured by using a film forming process, for example. The manufacturing thereof is briefly described as follows. The insulating layer 201, the first electrode 130, the piezoelectric body 140, the second electrode 150, the insulating layer 240, the wiring layer 250, and the protective layer (coating portion) 260 are formed, in this order, on a Si wafer as the substrate 200. The shape of each substrate 200 is formed by etching, and at the same time, the gap 205 between the vibrating portion 210 and the support 220 is formed, and the recess 216 (FIG. 2) for attaching the protrusion 103 is formed. Accordingly, the plurality of piezoelectric vibrators 102 can be formed on one Si wafer. The two piezoelectric vibrators 102 are disposed so that the substrates 200 face the outer side, the piezoelectric elements 110a to 110e face the inner side, and the members using the same reference numeral are in a plane symmetry, the coating portions 260 of the two piezoelectric vibrators 102 are bonded to each other with the adhesive layer 270, and the protrusion 103 is bonded over the recess 216 of the two substrates 200 with an adhesive. Accordingly, it is possible to manufacture the piezoelectric vibrator unit 101. The piezoelectric actuator 100 can be manufactured by laminating the plurality of (two in this example) piezoelectric vibrator units 101 on each other. The plurality of piezoelectric vibrator units 101 can be laminated on each other by bonding using an adhesive (not shown), for example. The plurality of piezoelectric vibrator units 101 can also be laminated on each other in a housing (not shown).

As the insulating layers 201 and 240, a $SiO_2$ layer formed by performing thermal oxidation of a surface of the substrate 200 can be used, for example. As the insulating layer 201, an organic material such as alumina ($Al_2O_3$), acryl, or polyimide can also be used. In a case where the substrate 200 is an insulator, a step of forming the insulating layer 201 can be omitted.

As a material of the electrodes 130 and 150, an arbitrary material having high conductivity such as aluminum (Al), nickel (Ni), gold (Au), platinum (Pt), iridium (Ir), or copper (Cu) can be used. The electrodes 130 and 150 can be formed by sputtering, for example, and the patterning can be performed by etching, for example.

As a material of the piezoelectric body 140, an arbitrary material exhibiting a piezoelectric effect such as ceramic having $ABO_3$ type Perovskite structure can be used. Examples of ceramic having $ABO_3$ type Perovskite structure can include lead zirconate titanate (PZT), barium titanate, lead titanate, potassium niobate, lithium niobate, lithium tantalate, sodium tungstate, zinc oxide, barium strontium titanate (BST), strontium bismuth tantalate (SBT), lead metaniobate, lead zinc niobate, and lead scandium niobate. A material exhibiting a piezoelectric effect other than the ceramic, for example, polyvinylidene fluoride or a crystal can also be used, for example.

The formation of the piezoelectric body 140 may be performed using a bulk material or may be performed by using a sol-gel method, for example. That is, a sol-gel solution of a piezoelectric material is added dropwise on the substrate 200 (first electrode 130), and a thin film of the sol-gel solution is formed on the first electrode 130 by rapidly rotating the substrate 200. Then, a first layer of a piezoelectric material is formed on the first electrode 130 by calcining the sol-gel solution at a temperature of 200° C. to 300° C. After that, the cycle of the adding of the sol-gel solution dropwise, rapid rotation, and calcining is repeated several times, and accordingly, a piezoelectric layer is formed on the first electrode 130 with a desired thickness. A thickness of a layer of a piezoelectric body formed by one cycle depends on viscosity of the sol-gel solution or a rotation rate of the substrate 200, and is approximately 50 nm to 150 nm. After forming the piezoelectric layer having a desired thickness, the piezoelectric layer is sintered at a temperature of 600° C. to 1,000° C. to form a piezoelectric body 140. When a thickness of the piezoelectric body 140 after the sintering is 50 nm (0.05 μm) to 20 μm, it is possible to realize the miniaturized piezoelectric actuator 100. When the thickness of the piezoelectric body 140 is equal to or greater than 0.05 μm, it is possible to generate a significantly great force in accordance with expansion and contraction of the piezoelectric body 140. When the thickness of the piezoelectric body 140 is equal to or smaller than 20 μm, it is possible to generate a significantly great force, even when a voltage applied to the piezoelectric body 140 is equal to or smaller than 600 V. As a result, it is possible to configure a driving circuit (not shown) for driving the piezoelectric actuator 100 with a low-cost element. The thickness of the piezoelectric body may be equal to or greater than 400 nm, and in this case, it is possible to increase a force generated by the piezoelectric element. The temperature and the time of the calcining or sintering are merely an example and suitably selected in accordance with the piezoelectric material. The thickness of the piezoelectric body 140 may be equal to or greater than 20 μm.

The patterning of the piezoelectric body 140 can be performed by performing ion milling using an argon ion beam. Instead of performing the patterning using the ion milling, the patterning may be performed by other arbitrary patterning methods (for example, dry etching using chlorine-based gas).

The wiring layer 250 can be formed with copper or brass. The wiring layer 250 can be formed by sputtering, for example, and a wiring can be formed in the wiring layer 250 by patterning. The patterning of a wiring can be performed by etching, for example.

The piezoelectric actuator 100 includes four piezoelectric vibrators 102 (FIG. 3). The piezoelectric elements 110a to 110e of each piezoelectric vibrator 102 are divided into three groups. A first group includes two piezoelectric elements 110a and 110d. A second group includes two piezoelectric elements 110b and 110c. A third group includes only one piezoelectric element 110e. The piezoelectric elements 110a and 110d in the first groups of the four piezoelectric vibrators 102 are connected to each other in parallel in the piezoelectric vibrator and connected to each other in parallel between the piezoelectric vibrators, and the piezoelectric elements are connected to the signal generation unit 360. The piezoelectric elements 110b and 110c in the second groups of the four piezoelectric vibrators 102 are connected to each other in parallel in the piezoelectric vibrator and connected to each other in parallel between the piezoelectric vibrators, and the piezoelectric elements are connected to the signal generation unit 360. The piezoelectric elements 110e in the third groups of the four piezoelectric vibrators 102 are connected to each other in parallel between the piezoelectric vibrators and the piezoelectric elements are connected to the signal generation unit 360.

The piezoelectric actuator 100 applies a driving signal of an AC voltage or an undulating voltage (also referred to as a "driving voltage") periodically changes, between the first electrode 130 and the second electrode 150 of the predetermined piezoelectric elements of each piezoelectric vibrator 102, for example, the piezoelectric elements 110a and 110d of the plurality of first groups connected in parallel, from the signal generation unit 360 (FIG. 1), to cause ultrasonic vibration of the piezoelectric actuator 100, and the rotor 310 coming into contact with the protrusion 103 can be rotated in a predetermined direction. Here, the "undulating voltage" means a voltage obtained by applying DC offset to an AC voltage and a direction of the voltage (electric field) of the undulating voltage is a direction from one electrode towards the other electrode. The direction of the current is preferably from the second electrode 150 towards the first electrode 130, instead of the direction from the first electrode 130 towards the second electrode 150. The rotor 310 coming into contact with the protrusion 103 can be rotated in the reverse direction by applying a driving voltage between the first electrode 130 and the second electrode 150 of the piezoelectric elements 110b and 110c of the plurality of second groups connected in parallel.

Figure 4:
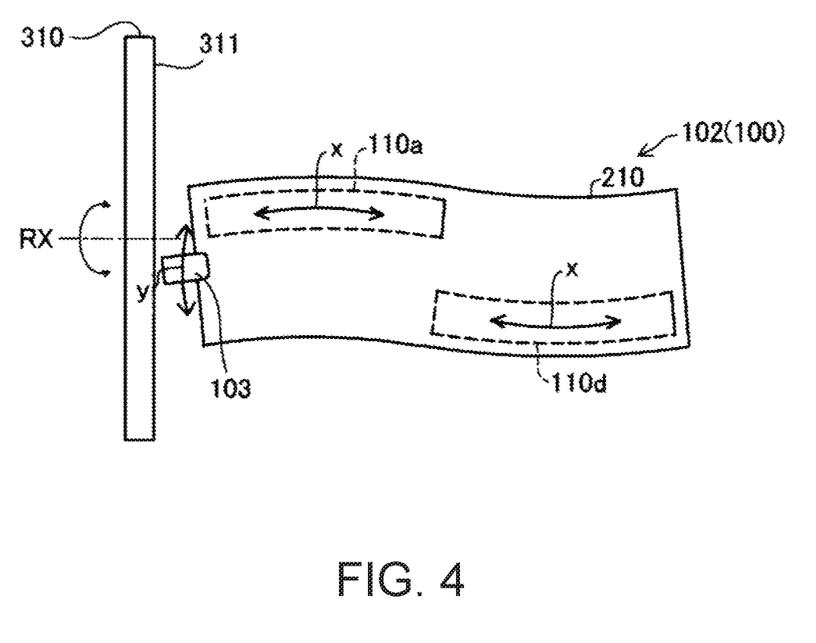
FIG. 4 is an explanatory diagram showing an example of an operation of the piezoelectric actuator.

FIG. 4 is an explanatory diagram showing an example of an operation of the piezoelectric actuator 100. FIG. 4 shows a state in which a driving voltage is applied to the piezoelectric elements 110a and 110d of the first group, and the piezoelectric elements 110a and 110d of the first group expands and contracts in a direction of an arrow x. This vibration is transmitted to the vibrating portion 210 of the substrate 200, and the vibrating portion 210 is vibrated (bending vibration) to be bent in the plane of the vibrating portion 210 and deformed in a meander shape (S shape). The protrusion 103 performs a reciprocating motion or an elliptic motion in a direction of an arrow y (width direction of the vibrating portion 210) in the plane of the piezoelectric vibrator 102. As a result, the rotor 310 rotates around the central axis RX in a predetermined direction. In a case of applying a driving voltage to the piezoelectric elements 110b and 110c (FIG. 2) of the second groups, the rotor 310 is rotated in the reverse direction. When a driving voltage is applied to the piezoelectric elements 110e of the third group in the center, the piezoelectric actuator 100 expands and contracts in a longitudinal direction, and accordingly, a force applied to the rotor 310 from the protrusion 103 can be greater. JP-A-2004-320979 (or corresponding U.S. Pat. No. 7,224,102) discloses the operation of the piezoelectric actuator 100, and the content disclosed is incorporated as a reference.

A frequency (also referred to as a "driving frequency") of a driving voltage applied to the piezoelectric elements 110a to 110e is set to a resonance frequency of the piezoelectric actuator 100 or a frequency close thereto, in advance, in order to improve output characteristics of the piezoelectric actuator 100, by efficiently using the vibration of the piezoelectric vibrator 102.

In the following description, the piezoelectric elements 110a and 110d of the plurality of first groups, the piezoelectric elements 110b and 110c of the second groups, and the piezoelectric elements 110e of the third groups of the four piezoelectric vibrators 102 of the piezoelectric actuator 100 which are connected in parallel, are not particularly distinguished and the plurality of piezoelectric elements connected in parallel in the same group will be described as the "piezoelectric elements 110".

Figure 5:
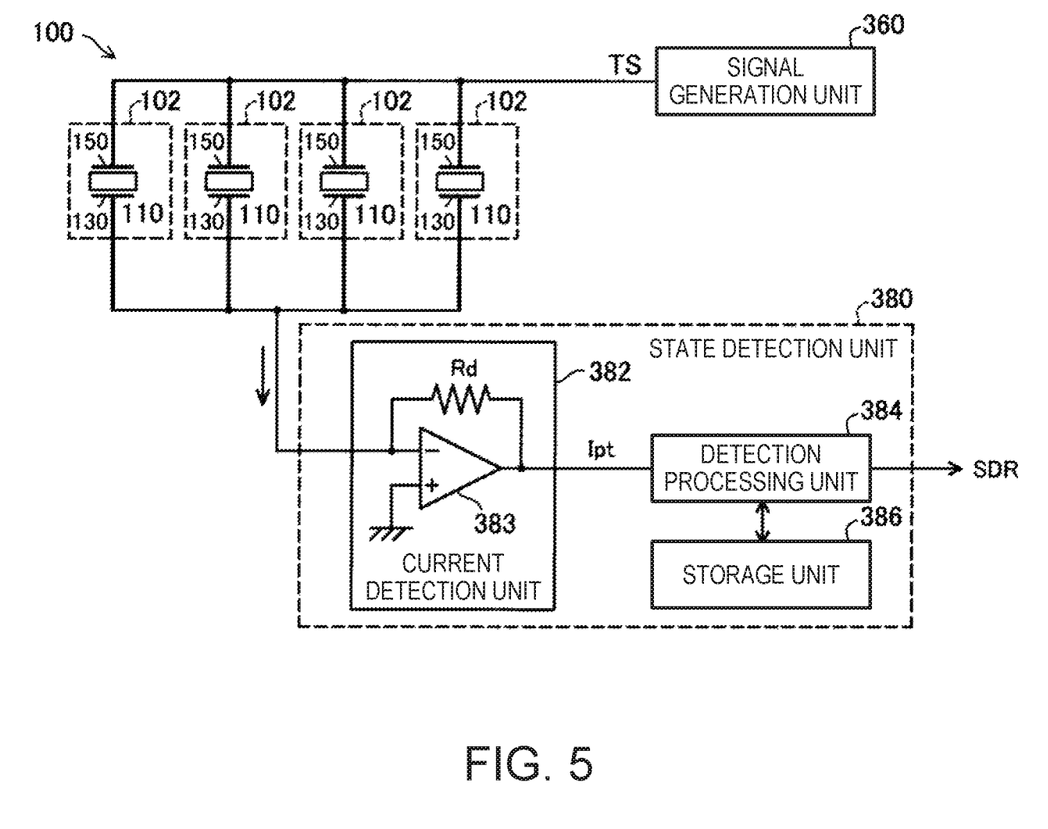
FIG. 5 is an explanatory diagram showing an internal configuration of a state detection unit.

FIG. 5 is an explanatory diagram showing an internal configuration of the state detection unit 380 (FIG. 1). The state detection unit 380 includes a current detection unit 382, a detection processing unit 384, and a storage unit 386. The current detection unit 382 connects a negative input terminal and an output terminal of an operational amplifier 383 with a current detection resistor Rd, and is configured with an I-V converter in which a positive input terminal is grounded. The I-V converter outputs a voltage difference between the current detection resistors Rd generated due to the input current as a voltage corresponding to the input current. The current detection unit 382 detects a current flowing to the plurality of piezoelectric elements 110 from a state inspection signal TS input to the plurality of piezoelectric elements 110 of the piezoelectric actuator 100, and detects a current Ipt detected as a state detection signal. The detection processing unit 384 detects the state of the plurality of piezoelectric elements 110 based on the current Ipt as the state detection signal, as will be described later. A determination value used for detecting the state of the plurality of piezoelectric elements 110 is stored in the storage unit 386.

Figure 6:
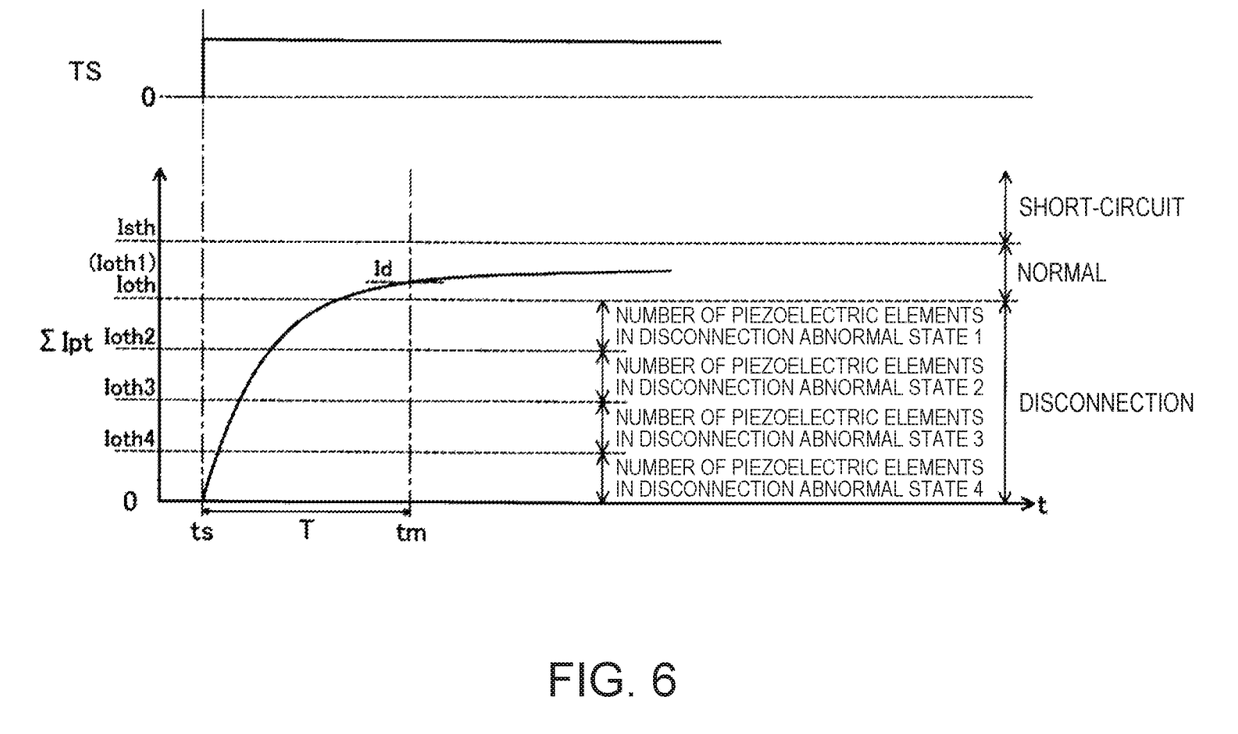
FIG. 6 is an explanatory diagram showing state detection of a plurality of piezoelectric elements in a detection processing unit.

FIG. 6 is an explanatory diagram showing state detection of the plurality of piezoelectric elements 110 in the detection processing unit 384. The signal generation unit 360 (FIG. 5) inputs a step-wise voltage signal to the plurality of piezoelectric elements 110 connected in parallel, as the state inspection signal TS. The detection processing unit 384 (FIG. 5) acquires an integrated current $\Sigma$Ipt obtained by integrating the current Ipt as the state detection signal detected by the current detection unit 382, and acquires a current value of the integrated current $\Sigma$Ipt at a time tm when a certain time T has elapsed from a start time is of the state inspection signal TS, as a state detection value Id. The detection processing unit 384 detects the state of the plurality of piezoelectric elements based on the state detection value Id. Specifically, the detection processing unit detects whether all of the piezoelectric elements 110 are in a normal state, at least one piezoelectric element 110 is in a short-circuit abnormal state, or at least one piezoelectric element is in a disconnection abnormal state.

The determination conditions of the normal state, the short-circuit abnormal state, and the disconnection abnormal state are as follows.

[Normal state]

Disconnection determination value Ioth$\leq$state detection value Id$\leq$short-circuit determination value Isth

[Short-circuit abnormal state]

State detection value Id>short-circuit determination value Isth

[Disconnection abnormal state]

State detection value Id<disconnection determination value Ioth

In a case of the disconnection abnormal state, the current Ipt as the detection state signal detected by the current detection unit 382 decreases in proportional to the number of piezoelectric elements in the disconnection abnormal state, and accordingly, the number of piezoelectric elements in the disconnection abnormal state can be detected based on the state detection value Id.

In a case of the four piezoelectric elements 110 as in this example, the number of piezoelectric elements in the disconnection abnormal state can be detected in accordance with the following determination conditions.

[Number in disconnection abnormal state: 1]

First disconnection determination value Ioth1>state detection value Id$\geq$second disconnection determination value Ioth2

Here, the first disconnection determination value Ioth1 is equivalent to the disconnection determination value Ioth.

[Number in disconnection abnormal state: 2]

Second disconnection determination value Ioth2>state detection value Id$\geq$third disconnection determination value Ioth3

[Number in disconnection abnormal state: 3]

Third disconnection determination value Ioth3>state detection value Id$\geq$fourth disconnection determination value Ioth4

[Number in disconnection abnormal state: 4]

Fourth disconnection determination value Ioth4>state detection value Id$\geq$0

Here, the current flowing to the piezoelectric element 110 in accordance with the step-wise state inspection signal TS has response characteristics based on a time constant $\tau$ (for example, represented by the product RC of a capacitive component C and an impedance component R of an equivalent circuit of the piezoelectric element 110) showing step response characteristics of the piezoelectric element 110, and this is also same for the integrated current $\Sigma$Ipt. Therefore, in a case where a certain time T is set as a response waiting time (for example, 3$\tau$) which is predetermined based on the time constant $\tau$, a standard integrated current value of the integrated current $\Sigma$Ipt at the time tm when the certain time T has elapsed is set as a reference, a value obtained by considering a margin to a current value assumed in a case where at least one piezoelectric element 110 is in the short-circuit abnormal state may be set as a short-circuit determination value Isth. In addition, a value obtained by considering a margin to an integrated current value assumed in a case where one piezoelectric element 110 is in the disconnection abnormal state may be set as the disconnection determination value Ioth. The range of the short-circuit determination value Isth from the disconnection determination value Ioth can be set as 0.875 to 1.125, in terms of a ratio with respect to the reference integrated current value. These determination values may be acquired in advance and set in the storage unit 386.

The second to fourth disconnection determination values Ioth2 to Ioth4 may be respectively set based on a value obtained by considering a margin to the integrated current value assumed in a case where one piezoelectric element 110 is in the disconnection abnormal state. These determination values may also be acquired in advance and set in the storage unit 386.

The control circuit 330 corresponding to one piezoelectric actuator 100 among the plurality of piezoelectric actuators 100 has been described, but the operation of the control circuit 330 corresponding to the other piezoelectric actuator 100 is performed in the same manner.

As described above, in the first embodiment, the state of the plurality of piezoelectric elements 110 of the piezoelectric actuator 100 connected in parallel can be detected by using the current flowing to the plurality of piezoelectric element 110 in accordance with the input step-wise state inspection signal as state detection signals showing the state of the plurality of piezoelectric elements 110, and the state of the plurality of piezoelectric elements 110 can be specifically detected whether piezoelectric elements are in the normal state, at least one piezoelectric element is in the short-circuit abnormal state, or at least one piezoelectric element is in the disconnection abnormal state, based on the detected state detection signal. The number of the piezoelectric elements in the disconnection abnormal state can also be detected.

One control circuit 330 commonly used for the plurality of piezoelectric actuators 100 may be provided, instead of providing the plurality of control circuits 330 corresponding to the plurality of piezoelectric actuators 100. In this case, the one common control circuit 300 is provided for the plurality of piezoelectric actuators 100 and can detect the state of the plurality of piezoelectric elements 110 connected in parallel. One piezoelectric actuator 100 and the control circuit 330 may be provided.

Figure 7:
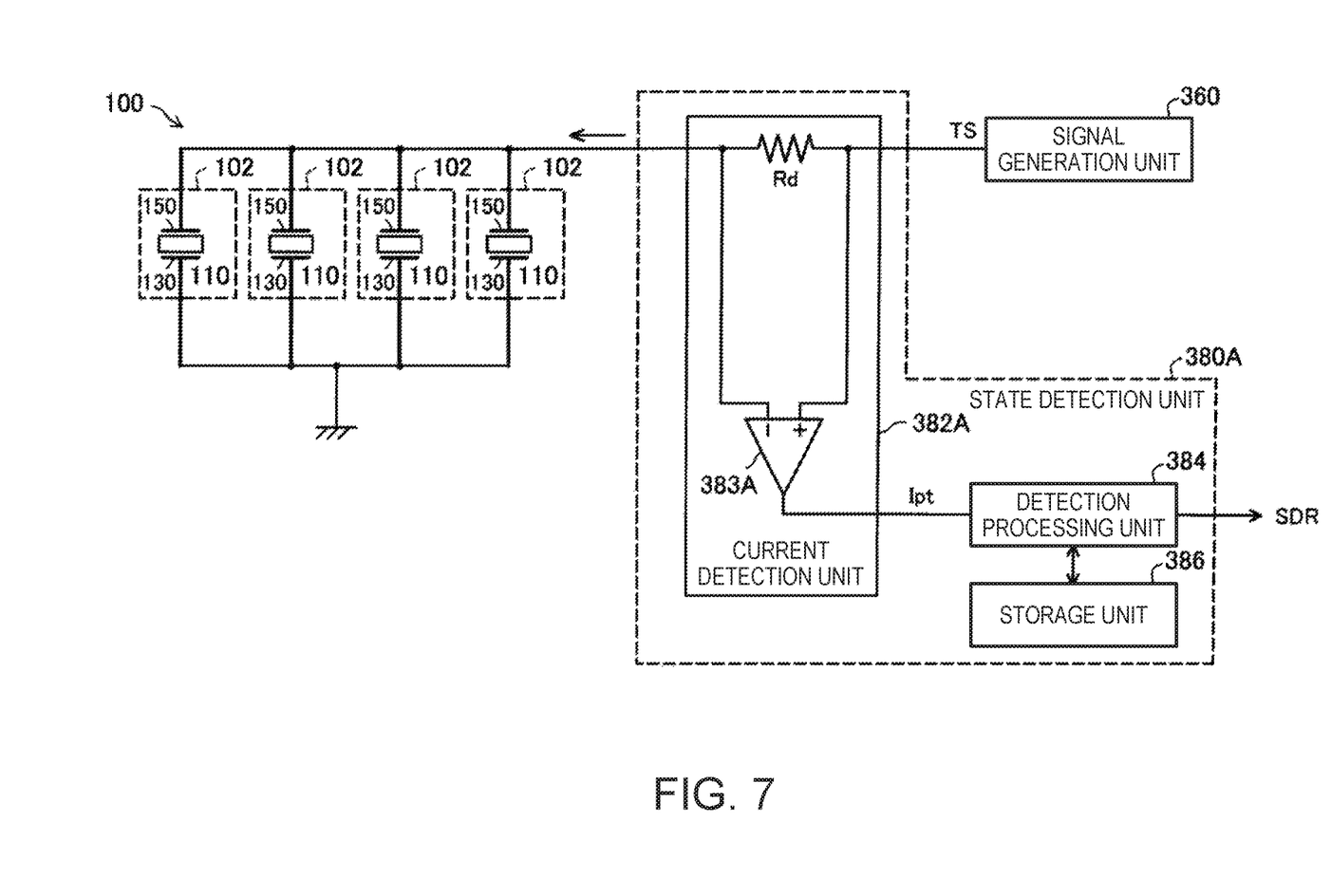
FIG. 7 is an explanatory diagram showing a state detection unit of a modification example.

FIG. 7 is an explanatory diagram showing a state detection unit 380A of a modification example. A current detection unit 382A may be used instead of the current detection unit 382 of the state detection unit 380 (FIG. 5).

This current detection unit 382A includes the current detection resistors Rd between the signal generation unit 360 and the plurality of piezoelectric elements 110 of the piezoelectric actuator 100 connected in parallel, detects a voltage difference between the current detection resistors Rd generated due to the currents flowing to the plurality of piezoelectric elements 110 by a differential amplifier 383A, and outputs the detected voltage difference as a voltage corresponding to the current flowing to the plurality of piezoelectric elements 110. That is, in the same manner as in the current detection unit 382, the current detection unit 382A also detects the current flowing to the plurality of piezoelectric elements 110 from the state inspection signal TS input to the plurality of piezoelectric elements 110 of the piezoelectric actuator 100, and can be output the detected current Ipt as the state detection signal.

Accordingly, even when the state detection unit 380 of the first embodiment is set as the state detection unit 380A of the modification example, the state of the plurality of piezoelectric elements 110 of the piezoelectric actuator 100 connected in parallel can be detected by using the current flowing to the plurality of piezoelectric element 110 in accordance with the input step-wise state inspection signal as state detection signals showing the state of the plurality of piezoelectric elements 110, and the state of the plurality of piezoelectric elements 110 can be specifically detected whether piezoelectric elements are in the normal state, at least one piezoelectric element is in the short-circuit abnormal state, or at least one piezoelectric element is in the disconnection abnormal state, based on the detected state detection signal. The number of the piezoelectric elements in the disconnection abnormal state can be determined.

The piezoelectric actuator 100 has been described with an example of the configuration including the two piezoelectric vibrator units 101 laminated on each other. However, there is no limitation and one or more piezoelectric vibrators 102 may be provided. The piezoelectric vibrator 102 has been described with an example of the configuration including the piezoelectric elements 110a and 110d of the first group, the piezoelectric elements 110b and 110c of the second group, and the piezoelectric element 110e of the third group. However, there is no limitation, and any piezoelectric elements among the piezoelectric elements 110a and 110d of the first group, the piezoelectric elements 110b and 110c of the second group, and the piezoelectric element 110e of the third group may be provided or a combination of any two piezoelectric elements may be provided. However, in a case of one piezoelectric actuator 100, it is necessary to provide the plurality of piezoelectric elements 110 connected in parallel, in the piezoelectric actuator 100.

These various modification examples can be applied in the following embodiments, in the same manner.

As described above, the integrated current ΣIpt flowing to the piezoelectric element 110 in accordance with the step-wise state inspection signal TS has response characteristics increasing in accordance with the time constant τ showing the step response characteristics of the piezoelectric element 110, and accordingly, the state detection value Id shows the state of increasing of the integrated current ΣIpt flowing to the plurality of piezoelectric elements 110 at the time tm when the certain time T has elapsed from the start time ts of the state inspection signal TS. Accordingly, it is possible to detect the state of the plurality of piezoelectric elements 110, by comparing a reference value and the state detection value Id of the integrated current ΣIpt determined from the time constant τ of the plurality of piezoelectric elements 110 at time tm when the certain time T has elapsed from the start time ts of the state inspection signal TS to each other. In this case, the short-circuit determination value Isth, the disconnection determination value Ioth (first disconnection determination value Ioth1), the second disconnection determination value Ioth2, the third disconnection determination value Ioth3, and the fourth disconnection determination value Ioth4 stored in the storage unit 386 may be respectively set as values showing a relationship of the state of the plurality of piezoelectric elements 110 and the state of increasing of the integrated current ΣIpt, at time tm when the certain time T has elapsed from the start time is of the state inspection signal TS.

B. Second Embodiment

Figure 8:
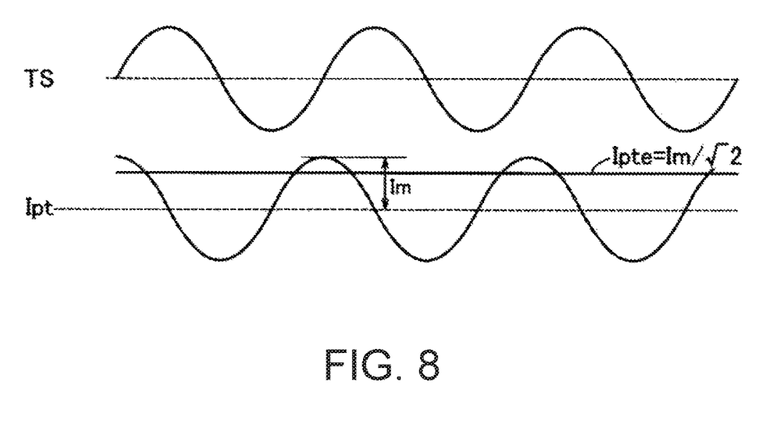
FIG. 8 is an explanatory diagram showing a current as a state inspection signal and a current as a state detection signal of a second embodiment.

FIG. 8 is an explanatory diagram showing the state inspection signal TS and the current Ipt as a state detection signal of a second embodiment. In the second embodiment, the signal generation unit 360 (FIG. 5) outputs a sinusoid voltage signal as the state inspection signal TS input to the plurality of piezoelectric elements 110. In this case, the current Ipt as the state detection signal detected by the current detection unit 382 (FIG. 5) also becomes a sinusoid current signal.

The detection processing unit 384 (FIG. 5) acquires an effective current value Ipte ($=Im/\sqrt{2}$) from the current Ipt as the state detection value Id. Im represents an amplitude of the sinusoid current Ipt. The detection processing unit 384 detects the state of the plurality of piezoelectric elements 110 based on the state detection value Id, in the same manner as in the first embodiment. However, the short-circuit determination value Isth, the disconnection determination value Ioth (first disconnection determination value Ioth1), the second disconnection determination value Ioth2, the third disconnection determination value Ioth3, and the fourth disconnection determination value Ioth4 of the second embodiment may be set as values obtained by considering a margin to the effective current value assumed in each case, by setting the standard effective current value as a reference.

In the second embodiment, the state of the plurality of piezoelectric elements 110 of the piezoelectric actuator 100 connected in parallel can be detected by using the current flowing to the plurality of piezoelectric element 110 in accordance with the input sinusoid state inspection signal as state detection signals showing the state of the plurality of piezoelectric elements 110, and the state of the plurality of piezoelectric elements 110 can be specifically detected whether piezoelectric elements are in the normal state, at least one piezoelectric element is in the short-circuit abnormal state, or at least one piezoelectric element is in the disconnection abnormal state, based on the detected state detection signal. The number of the piezoelectric elements in the disconnection abnormal state can also be detected.

C: Embodiment of Apparatus Using Ultrasonic Motor

The ultrasonic motor described above can apply great force to a member to be driven by using resonance and can be applied to various devices. The ultrasonic motor can be used as a driving device in various apparatuses such as a robot (including electronic component conveying apparatus (IC handler)), a hand (including finger assisting apparatus), a pump for medication, a calendar advancing apparatus of a clock, and a printing apparatus (for example, paper feeding mechanism), for example. Hereinafter, representative embodiments will be described.

Figure 9:
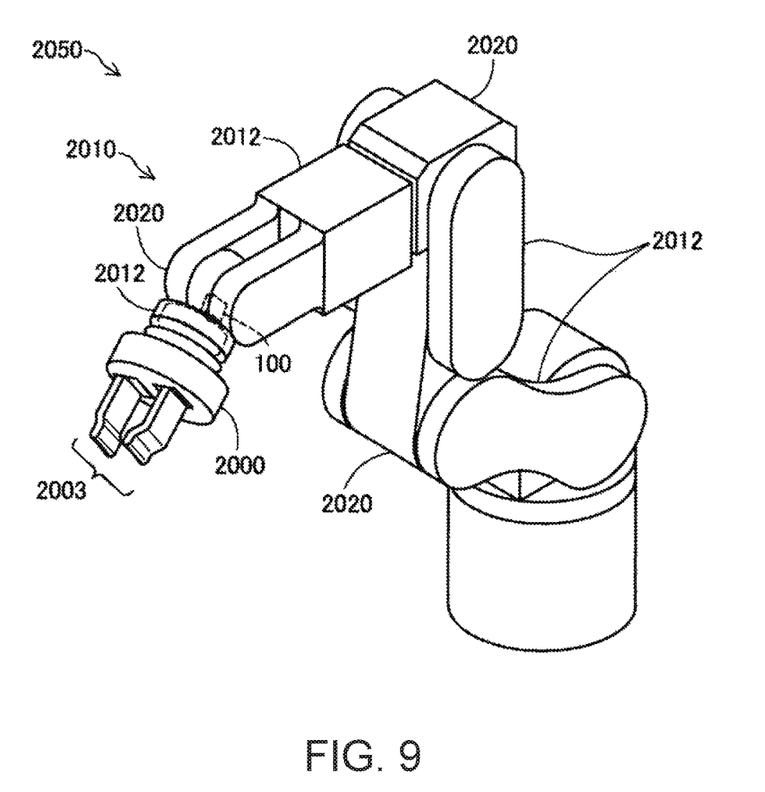
FIG. 9 is an explanatory diagram showing an example of a robot using an ultrasonic motor.

FIG. 9 is an explanatory diagram showing an example of a robot 2050 using the ultrasonic motor described above. The robot 2050 includes an arm 2010 (also referred to as an "arm portion") which includes a plurality of linking portions 2012 (also referred to as "linking members") and a plurality of joints 2020 which are connected between the linking portions 2012 to be rotated or curved. The ultrasonic motor described above is embedded in each joint 2020, and it is possible to rotate or curve the joint 2020 by an arbitrary angle using the ultrasonic motor. FIG. 9 shows the piezoelectric actuator 100 included in the ultrasonic motor. A hand 2000 is connected to an end of the arm 2010. The hand 2000 includes a pair of grasping portions 2003. The piezoelectric actuator 100 is embedded in the hand 2000, and it is possible to open and close the grasping portions 2003 using the piezoelectric actuator 100 to grasp an object. In addition, the ultrasonic motor 300 is also provided between the hand 2000 and the arm 2010, and it is possible to rotate the hand 2000 with respect to the arm 2010 using the ultrasonic motor 300.

Since the ultrasonic motor used in the robot 2050 can detect the state of the plurality of piezoelectric elements 110 included in the piezoelectric actuator 100, it is possible to easily detect the state of the ultrasonic motor.

Figure 10:
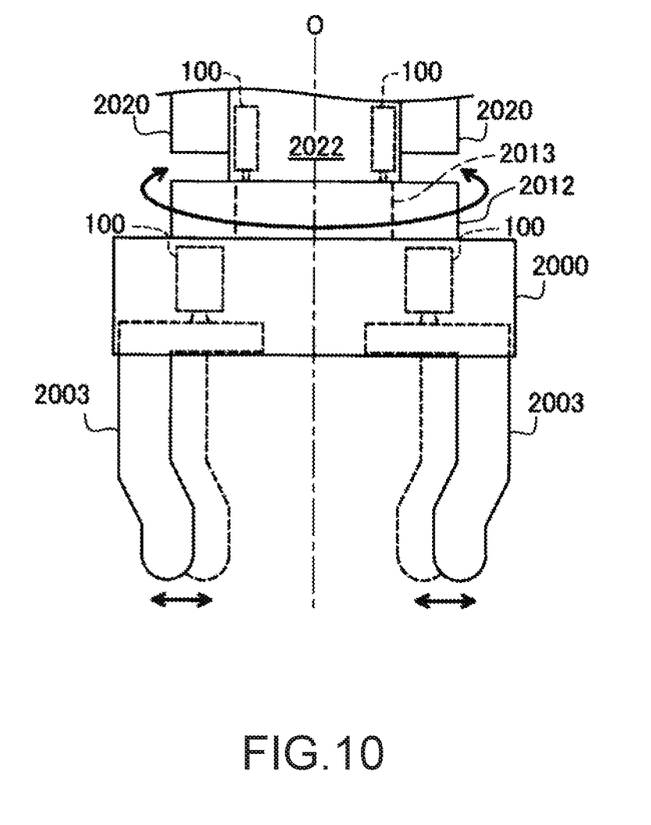
FIG. 10 is an explanatory diagram of a hand of the robot using the ultrasonic motor.

FIG. 10 is an explanatory diagram of a wrist part of the robot 2050 shown in FIG. 9. The wrist joints 2020 interpose a wrist rotation portion 2022 and a wrist linking portion 2012 is attached to the wrist rotation portion 2022 to be rotated around a center axis O of the wrist rotation portion 2022. The wrist rotation portion 2022 includes the ultrasonic motor. When the ultrasonic motor rotates the rotor 2013 by the piezoelectric actuator 100, the rotor 2013 rotates the fixed wrist linking portion 2012 and the hand 2000 around the center axis O. The plurality of grasping portions 2003 are provided to stand on the hand 2000. A proximal end portion of the grasping portion 2003 can move in the hand 2000 and the piezoelectric actuator 100 is mounted in a base portion of the grasping portion 2003. Accordingly, by operating the piezoelectric actuator 100, it is possible to grasp a target by moving the grasping portion 2003.

The robot is not limited to a single arm robot, and the ultrasonic motor can also be applied to a multi-arm robot having two or more arms. Here, in addition to the ultrasonic motor, an electric power line for applying power to various devices such as a force sensor or a gyro sensor or a signal line for transmitting signals to the devices is included in the wrist joints 2020 or the hand 2000, and an extremely large number of wirings are necessary. Accordingly, it was extremely difficult to dispose wirings in the joints 2020 or the hand 2000. However, since the ultrasonic motor of the embodiment described above can decrease a driving current, compared to a general electric motor or a piezoelectric driving device of the related art, it is possible to dispose wirings even in a small space such as the joint 2020 (particularly, a joint on the edge of the arm 2010) or the hand 2000.

In the above description, the robot 2050 including the hand 2000 has been described as an example, but the hand 2000 may not be provided as a part of the robot 2050 but may be configured as a single product.

Figure 11:
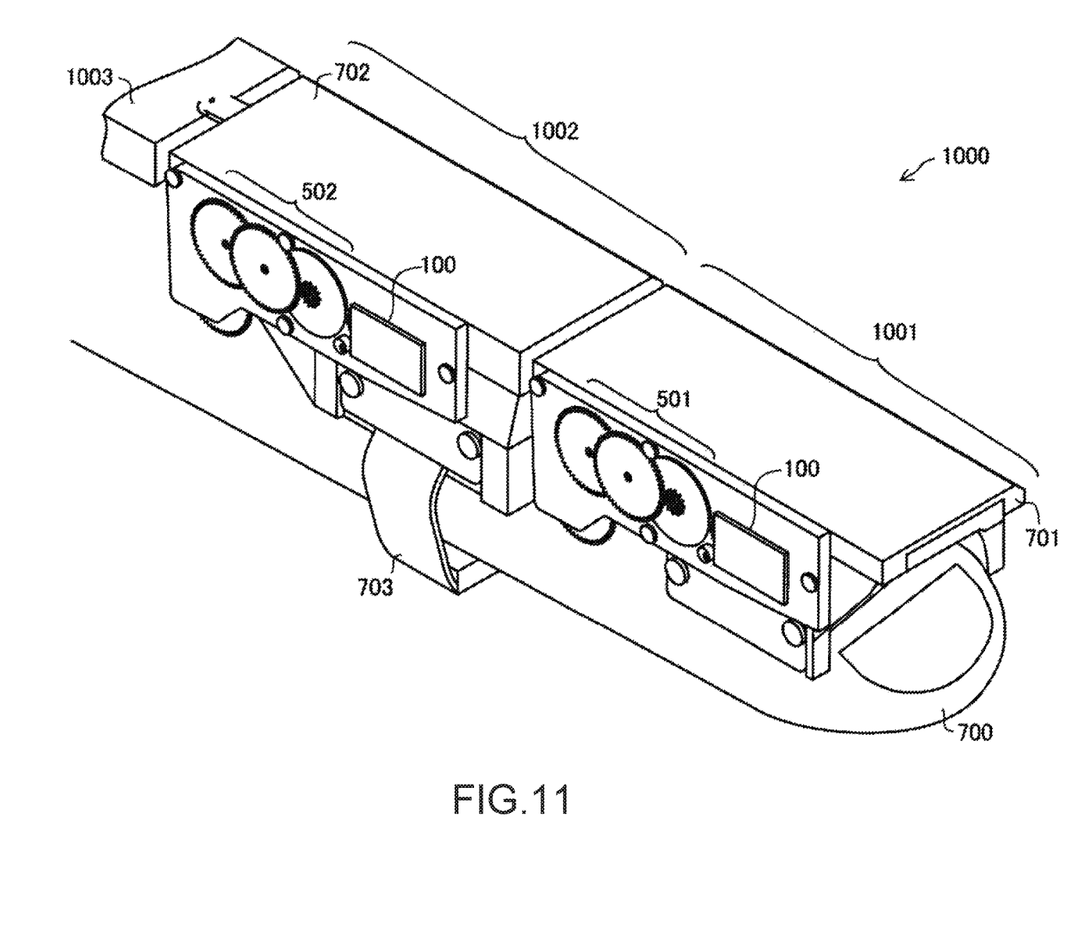
FIG. 11 is an explanatory diagram showing a finger assisting apparatus using the ultrasonic motor.

FIG. 11 is an explanatory diagram showing a finger assisting apparatus 1000 using the ultrasonic motor described above. The finger assisting apparatus 1000 includes a first finger assisting unit 1001, a second finger assisting unit 1002, and a base member 1003, and is attached to a finger 700. The first finger assisting unit 1001 includes the piezoelectric actuator 100 of the ultrasonic motor, a reduction gear 501 including the rotor corresponding to a body to be driven of the ultrasonic motor, and a finger support 701. The second finger assisting unit 1002 includes the piezoelectric actuator 100 of the ultrasonic motor, a reduction gear 502 including the rotor corresponding to a body to be driven of the ultrasonic motor, a finger support 702, and a band 703. The first finger assisting unit 1001 and the second finger assisting unit 1002 have substantially the same configuration, except for a band 703. The band 703 fixes the second finger assisting unit 1002 from the pad side of the finger 700. The band 703 is also provided in the first finger assisting unit 1001 but omitted in FIG. 11. The finger assisting apparatus 1000 assists bending and stretching of the finger 700 with the ultrasonic motor. In the embodiment, the finger assisting apparatus 1000 has been described as an apparatus that assists bending and stretching of the finger 700, but the hand and the finger assisting apparatus 1000 may be integrally formed using a hand of a robot, instead of the finger 700. In this case, the hand is driven by the ultrasonic motor and is bent and stretched.

The ultrasonic motor used in the finger assisting apparatus 1000 can detect the state of the plurality of piezoelectric elements 110 included in the piezoelectric actuator 100, and accordingly, it is possible to easily detect the state of the ultrasonic motor.

Figure 12:
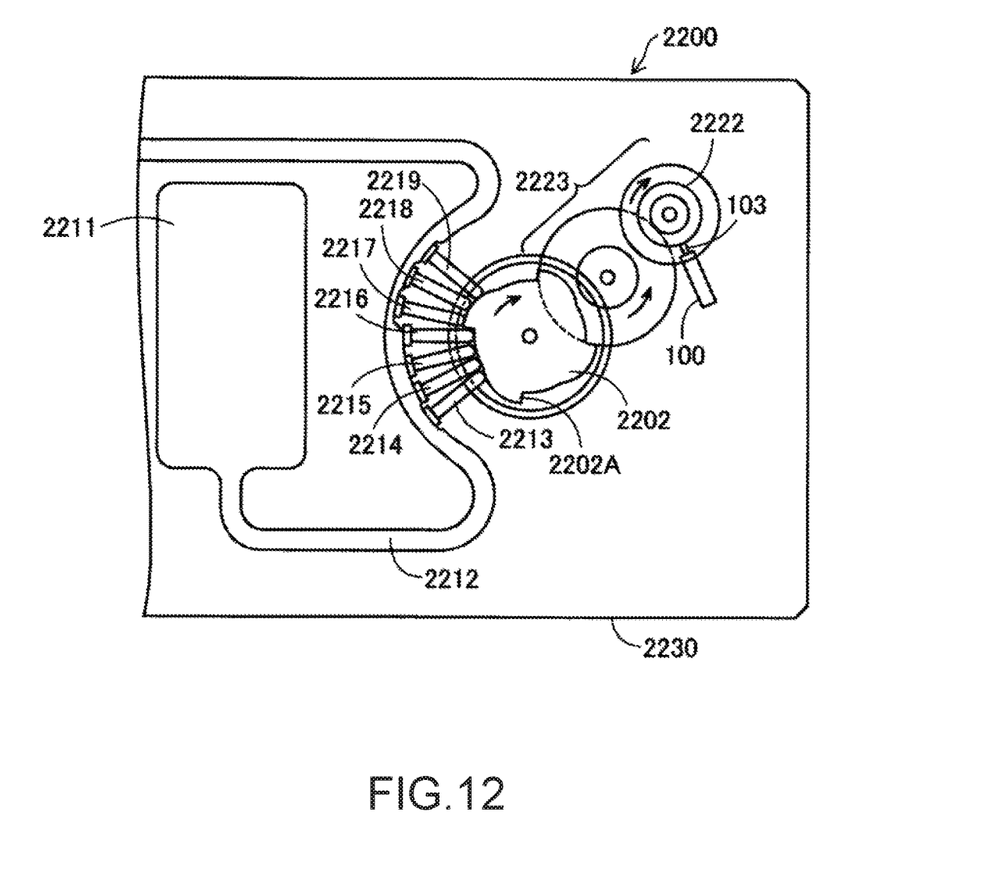
FIG. 12 is an explanatory diagram showing an example of a liquid feeding pump using the ultrasonic motor.

FIG. 12 is an explanatory diagram showing an example of a liquid feeding pump 2200 using the ultrasonic motor described above. The liquid feeding pump 2200 includes a reservoir 2211, a tube 2212, the piezoelectric actuator 100 of the ultrasonic motor, a rotor 2222 corresponding to a body to be driven of the ultrasonic motor, a deceleration transmission mechanism 2223, a cam 2202, and a plurality of fingers 2213, 2214, 2215, 2216, 2217, 2218, and 2219 in a case 2230. The reservoir 2211 is an accommodation portion which accommodates liquid which is a transportation target. The tube 2212 is a tube which transports the liquid sent from the reservoir 2211. The protrusion 103 of the piezoelectric actuator 100 is provided in a state of being pressed against a side surface of the rotor 2222 and the piezoelectric actuator 100 rotates the rotor 2222. A rotation force of the rotor 2222 is transmitted to the cam 2202 through the deceleration transmission mechanism 2223. The fingers 2213 to 2219 are members which block the tube 2212. When the cam 2202 is rotated, the fingers 2213 to 2219 are pressed to the outer side in a radial direction in order, by a protrusion 2202A of the cam 2202. The fingers 2213 to 2219 block the tube 2212 in order from the upstream side in a transportation direction (reservoir 2211 side). Accordingly, the liquid in the tube 2212 is transmitted to the downstream side in order. By doing so, it is possible to realize a small liquid feeding pump 2200 which can accurately feed an extremely small amount of liquid. The disposition of each member is not limited to that shown in the drawing. The members such as fingers or the like may not be provided and a ball or the like provided on the rotor 2222 may block the tube 2212. The liquid feeding pump 2200 described above can be used as a dosing apparatus which gives medication such as insulin to a human body. Here, by using the ultrasonic motor of the embodiment described above, a driving current can be decreased, compared to a case of a piezoelectric driving device of the related art, and accordingly, it is possible to reduce power consumption of the dosing apparatus. Thus, when the dosing apparatus is driven with a battery, the effects are particularly effective.

Since the ultrasonic motor using the liquid feeding pump 2200 can detect the state of the plurality of piezoelectric elements 110 included in the piezoelectric actuator 100, it is possible to easily detect the state of the ultrasonic motor.

The invention is not limited to the embodiments, the examples, and the modification examples described above, and can be realized with various configurations within a range not departing from a gist thereof. For example, technical features in the embodiments, the examples, and the modification examples corresponding to technical features in each aspect disclosed in the summary can be suitably replaced or combined, in order to solve some or all of the problems described above or achieve some or all of the effects described above. When the technical features are not described as necessary features in this specification, the technical features can be suitably removed.

The entire disclosure of Japanese Patent Application No. 2016-056604, filed Mar. 22, 2016 is expressly incorporated by reference herein.

What is claimed is:

1. A control circuit of a piezoelectric driving device comprising:
    a signal generation unit that inputs a state inspection signal to a plurality of piezoelectric elements connected to each other in parallel; and
    a state detection unit comprising a current detection unit, a detection processing unit, and a storage unit, the state detection unit detects a state of the plurality of piezoelectric elements based on a state detection signal generated from the plurality of piezoelectric elements in accordance with the state inspection signal, the state detection signal being proportional to a number of the plurality of piezoelectric elements,
    wherein the state detection signal is a current flowing to the plurality of piezoelectric elements in accordance with the state inspection signal,
    the current detection unit detects a current flowing to the plurality of piezoelectric elements, the current detection unit comprising a current to voltage converter that generates an integrated current value and provides the integrated current value to the detection processing unit,
    wherein the state detection unit acquires the integrated current value when a certain time of an integrated current obtained by integrating the current detected by the current detection unit has been elapsed from the time when the state inspection signal in a step-wise shape is input, as a state detection value, detects the state of the plurality of piezoelectric elements based on the state detection value, and outputs an inspection result indicative of the state of the plurality of piezoelectric elements to a host control device,
    wherein the detection processing unit detects the state of the plurality of piezoelectric elements by comparing the state detection value with a determination value based on a time constant showing step response characteristics of the plurality of piezoelectric elements.

2. The control circuit according to claim 1,
    wherein the state detection unit includes a storage unit that stores a relationship between the state detection value and the determination value.

3. The control circuit according to claim 1,
    wherein the state detection unit detects whether the state of the plurality of piezoelectric elements is in any state of a normal state, a short-circuit abnormal state, and a disconnection abnormal state, based on the state detection value.

4. A piezoelectric driving device comprising:
    a plurality of piezoelectric elements connected to each other in parallel; and
    the control circuit according to claim 1.

5. The control circuit according to claim 3,
    wherein the state detection unit detects the number of piezoelectric elements in the disconnection abnormal state among the plurality of piezoelectric elements, based on the state detection value.

6. The piezoelectric driving device according to claim 4, further comprising:
    a piezoelectric actuator including the plurality of piezoelectric elements,
    wherein the plurality of piezoelectric elements are laminated and disposed in a direction crossing a flat surface where the piezoelectric elements are formed.

7. An ultrasonic motor comprising:
    a body; and
    the piezoelectric driving device according to claim 4.

8. The piezoelectric driving device according to claim 6, further comprising:
    a plurality of the piezoelectric actuators.

9. A robot comprising:
    the ultrasonic motor according to claim 7.

10. A hand comprising:
    the ultrasonic motor according to claim 7.

11. A pump comprising:
    the ultrasonic motor according to claim 7.

* * * * *